United States Patent [19]

Shuto et al.

[11] Patent Number: 4,797,479

[45] Date of Patent: Jan. 10, 1989

[54] NUCLEOSIDE-PHOSPHOLIPID CONJUGATE

[75] Inventors: Satoshi Shuto; Hiromichi Ito; Kiyofumi Fukukawa; Hideo Sakakibara; Masatoshi Tsujino, all of Shizuoka, Japan

[73] Assignee: Toyo Jozo Kabushiki Kaisha, Shizuoka, Japan

[21] Appl. No.: 852,881

[22] Filed: Apr. 15, 1986

[30] Foreign Application Priority Data

Apr. 15, 1985 [JP] Japan ................................ 60-78283
Oct. 25, 1985 [JP] Japan ................................ 60-237695

[51] Int. Cl.$^4$ .................... C07H 19/10; C07H 19/20; C07D 473/00
[52] U.S. Cl. ........................................ 536/27; 536/28; 536/29; 544/276
[58] Field of Search ............................ 536/27, 28, 29; 544/276

[56] References Cited

U.S. PATENT DOCUMENTS 4,291,024 9/1987 Turcotte ..................... 536/29

FOREIGN PATENT DOCUMENTS 1238793 10/1982 Japan ..................... 536/27

OTHER PUBLICATIONS

Nucleosides, Nucleotides and Their Biological Application, 41st Event of FECS, MacCoss et al., pp. 46–47, Feb. 1981.
Ramirez et al., the Chemical Abstracts, 97 3933d, 1982.
Ramirez et al., the Chemical Abstracts, 97 145213j, (1982).
Ryu et al., J. Med. Chem., 25, 1322–1329, (1982).
"Cytotoxic Liponucleotide Analogs, I. Chemical Synthesis of CDP-Diacylglycerol Analogs Containing the Cytosine Arabinoside Moiety", *Biochimica et Biophysica Acta.*, 619 (1980) J. G. Turcotte et al., pp. 604–618.
"Cytotoxic Liponucleotide Analogs, II. Antitumor Activity of CDP-Diacylglycerol Analogs Containing the Cytosine Arabinoside Moiety", *Biochimica et Biophysica Acta.*, 619 (1980), J. G. Turcotte et al., pp. 619–631.
"Phospholipid–Nucleoside Conjugates, 3. Syntheses and Preliminary Biological Evaluation . . .", *J. Med. Chem.*, vol. 25, 1982, by Eung K. Ryu et al., pp. 1322–1329.

*Primary Examiner*—Ronald W. Griffin
*Assistant Examiner*—Jenny Tou
*Attorney, Agent, or Firm*—Young & Thompson

[57] ABSTRACT

A compound of the formula

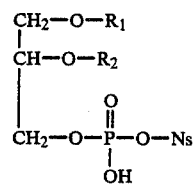

wherein $R_1$ and $R_2$ are long-chain fatty acid residue, and Ns is nucleoside residue selected from the group consisting of 5-fluorouridine-5'-yl, 5-fluoro-2'-deoxyuridine-5'-yl-, bredinin-5'-yl, tubercidine-5'-yl-, neplanocin A-6'-yl-, 5-fluorocytidine-5'-yl-, arabinosylcytosine-5'-yl, arabinocyl-5-fluorocytosine-5'-yl-, arabinosyladenine-5'-yl- and arabinosylthymine-5 '-yl-, and pharmacologically acceptable salts thereof, having antitumor activity.

5 Claims, No Drawings

NUCLEOSIDE-PHOSPHOLIPID CONJUGATE

This invention relates to novel nucleoside-phospholipid conjugates and salts thereof. More particularly the present invention pertains to a nucleoside-phospholipid conjugate of the formula [I]

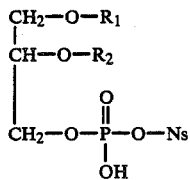

wherein $R_1$ and $R_2$ are long-chain fatty acid residue, and Ns is nucleoside residue selected from the group consisting of 5-fluorouridine-5'-yl, 5-fluoro-2'-deoxyuridine-5'-yl, bredinin-5'-yl-, tubercidine-5'-yl, neplanocin A-6'-yl-, 5-fluorocytidine-5'-yl-, arabinosylcytosine-5'-yl, arabinocyl-5-fluorocytosine-5'-yl, arabinosyladenine-5'-yl- and arabinosylthymine-5'-yl-, and salts thereof.

Nucleoside antitumor agents have been widely used as effective chemotherapeutics for neoplastic cells. In their application as antitumor-chemotherapeutics, however, several problems have been identified. For example, in a mechanism for the activity of nucleoside antineoplastic agent, phosphorylation of hydroxyl group at position-5' of nucleoside in vivo is essential for antitumor activity; the compound is decomposed to inactive substance by inactivation such as phosphorlysis and deamination; the resistance of tumor cells to antitumor agents is increased; and the agent is sometimes toxic to mitotic normal cells. Many kinds of nucleoside derivatives have been synthesized for overcoming the disadvantages of nucleoside antitumor agents.

CDP-diacylglycerol is known to have an important role as an intermediate in the biosynthesis of glycerophospholipid in vivo, and its analogue, arabinosylcytosine-phospholipid conjugate, which has antitumor activity, was chemically synthesized. [Biochem. Biophys. Acta, 619 (1980), J. Med. Chem., 1982, 25, 1322–1329].

As hereinabove explained, ribonucleoside is synthesized according to a chemical process and hence multistep synthetic processes are required. Therefore yield is low and processes are complicated. Furthermore, cytosine arabinoside has previously been known only as a nucleoside residue derived from phospholipid-nucleoside conjugate, and phospholipid-nucleoside complex having other types of nucleoside residue is required. For that purpose nucleosides other than cytosine arabinoside can be used, however chemical synthesis of these phospholipid-nucleoside complex requires multi-step synthetic processes with difficult reaction conditions and so practical chemical synthesis has been substantially impossible.

We have found a novel phospholipid-nucleoside complex can be synthesized by reacting L-glycerophospholipid with nucleoside in the presence of phospholipase D in which a primary hydroxyl group of the nucleoside and glycero-phospholipid is reacted.

An object of the present invention is to provide novel nucleoside-phospholipid conjugates of the formula [I]

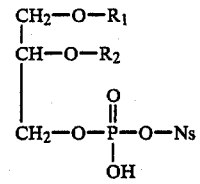

wherein $R_1$, $R_2$ and Ns have the same meanings as before.

Examples of glycerophospholipid are, for example, phosphatidylcholine of the formula [II]

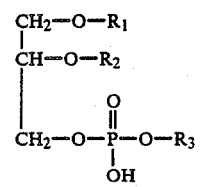

wherein $R_1$ and $R_2$ have the same meanings as before, and $-OR_3$ is choline residue.

In the phosphatidylcholine series glycerophospholipid, $R_1$ and $R_2$ are the same or different long chain fatty acid residues of carbon number 16–20. For example, long chain saturated fatty acid residues of $C_{16-20}$ such as palmitoyl, stearoyl or dodecanoyl, and long chain unsaturated fatty acid residues of $C_{16-20}$ having 1–4 unsaturated bonds, such as palmito-oleoyl, oleoyl, linoleoyl or arachidonyl, can be mentioned. Preferred examples are dipalmitoyl-phosphatidyl-choline wherein $R_1$ and $R_2$ are palmitoyl, dioleoyl-phosphatidyl choline wherein $R_1$ and $R_2$ are oleoyl, and dilinoleoyl-phosphatidyl choline wherein $R_1$ and $R_2$ are linoleoyl. Further natural phosphatidyl cholines are possible, wherein $R_1$ and $R_2$ are radyl of $C_{16-20}$ long chain fatty acid mixture. These phosphatidyl cholines are commercially available, or can by synthesized.

Examples of nucleoside are, for example, 5-fluorouridine (hereinafter called as FUR), 5-fluoro-2'-deoxyuridine (hereinafter called as FUDR), bredinin (4-carbamoyl-1-β-D-ribofuranosyl-imidazolium-5-oleate), tubercidine (7-deazaadenosine), neplanocin A (1-β-(9H-6-aminopurin-9-yl)-4-hydroxymethyl-4-cyclopentene-2α,3α-diol) (hereinafter called as NepA), 5-fluorocytidine (hereinafter called as FCR), arabinosylcytosine, arabinosyl-5-fluorocytosine, arabinosyladenine and arabinosylthymine.

Nucleoside-phospholipid complexes of the formula [I] can be obtained by reacting glycerophospholipid as before and nucleoside, optionally in the presence of metallic ion, with phospholipase D. A preferred example of phospholipase D is phospho-lipase D-P obtained from Streptomyces sp. AA586 FERM P-6100 (Jap. Pat. Unexam. Publ. No. 58-152481, Toyo Jozo Co., Catalogue No. P-39]. The amount of reagent is at least 0.1 unit phospholipase D per 1 mg of phosphatidyl choline, and is preferably 1–100 units. Examples of solvent which may be used are a bilayer solvent of organic solvent and water, for example a mixture of organic solvent such as ether, benzene or chloroform and buffer solution of pH 3–9, preferably pH 4–6. A general example of water soluble salt for generation of metallic ion is calcium chloride. Reaction temperature is generally 20°–60° C. and reaction time is 30 minutes to 5 hours.

The thus-obtained nucleoside-phospholipid conjugate can be purified by a partition method and/or silica-gel chromatography.

One-step synthesis of nucleoside-phospholipid complex of the present invention is illustrated as follows:

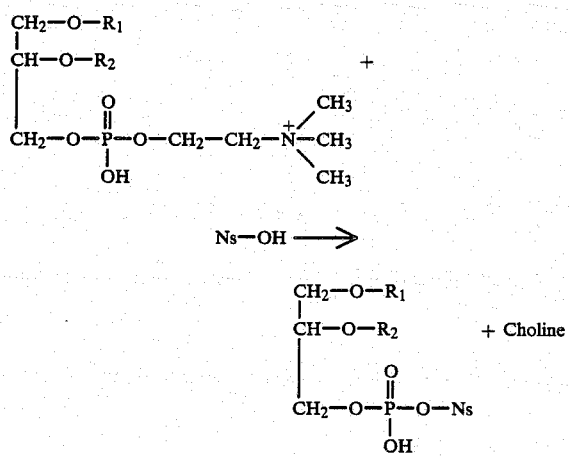

The nucleoside-phospholipid conjugate obtained hereinabove is a compound wherein the phosphate group in the phospholipid and the primary hydroxyl group at position-5' (or at position-6' in case of NepA) of the nucleoside are bonded. The thus-obtained product can be prepared as a non-toxic, pharmacologically acceptable salt thereof such as sodium salt, and can be administered in a general suspension in sterilized distilled water.

The thus-prepared nucleoside-phospholipid complex of the present invention has the advantages that: it is more lipophilic as compared with original nucleoside; it is not easily excreted, that is, it is more active for a longer time; it is not affected by inactivation such as phosphorlysis, deamination or reduction; it has higher affinity to cell membrane; antineoplactic nucelioside 5'-monophosphate is generated in cells; and it has long action and increased activity with low toxicity.

The novel nucleoside-phospholipid complexes of the present invention reveal marked antitumor activity in vivo, in addition to anti-metastatic activity of tumors, and anti-viral activity.

Antitumor activities against mouse leukemia P-388 carcinoma and Ehrlich ascites carcinoma are shown in the ensuing examples, according to the following list of specifications:

Antitumor activity

1. Samples: shown in Tables 1 and 2.
2. Animals: $BDF_1$ mice or ICR mice, aged 5-6 weeks, male, 5 mice in a group and 7 control mice.
3. Tumor cells: P-388 leukemic cells; $1 \times 10^6/0.2$ ml are inoculated intraperitoneally in $BDF_1$ mice. Ehrlich ascites carcinoma cells; $2 \times 10^6/0.2$ ml are inoculated intraperitoneally in ICR mice.
4. Preparation of samples and administration of drugs: Samples are suspended in Tris-HCl saline solution by sonication. 0.1 ml/10 g body weight is administered. Samples are stored at 4° C. in the dark. Administration: starting two days after inoculation of tumor, once a day for 2-7 days. Amount of dose is shown in the Tables.
5. Increase in life span (ILS) is calculated by the following equation:

$$ILS\ (\%) = \left( \frac{\text{mean life span (days); treated}}{\text{mean life span (span); control}} - 1 \right) \times 100$$

Experimental days: 35 days (partially 30 days) mice living in final days are not calculated in ILS.
6. Results:

TABLE 1

| | Nucleoside-phospholipid conjugate [I] | | Tumor cells | Admin. mg/kg (No. of administration) | ILS* (%) | 35 days survivals No./treated |
|---|---|---|---|---|---|---|
| Example | $R_1$ and $R_2$ | Ns | | | | |
| 1 | palmitoyl | FUR-5'-yl | P-388, | 30 (× 5) | 206.3 | 0/5 |
| | | | Ehrlich | 15 (× 5) | >88.0 | 2/5 |
| 2 | palmitoyl | NepA-6'-yl | P-388, | 50 (× 3) | >159.3 | 1/5 |
| | | | Ehrlich | 10 (× 7) | >68.7 | 2/5 |
| 4 | radyl | FUR-5'-yl | P-388 | 30 (× 5) | 98.3 | 0/5 |
| 3 | linoleoyl | FUR-5'-yl | P-388 | 15 (× 5) | 100.8 | 0/5 |
| | radyl | bredinin-5'-yl | Ehrlich | 50 (× 7) | 75.4 | 1/5 |

*Average survival date in control group;
P-388 leukemia: 7.57–7.79 days
Ehrlich ascites carcinoma: 15.14–15.43 days The following examples illustrate the present invention but are not to be construed as limiting.

EXAMPLE 1

5-fluorouridine (FUR, 4.0 g) was dissolved in 100 mM acetate buffer (pH 5.6, 20 ml) containing 100 mM $CaCl_2$ and stirred at 45° C. for 20 mins. Phospholipase D-P (10 mg, from Streptomyces, Toyo Jozo Co., specific activity 160 units/mg) and chloroform solution (30 ml) of dipalmitoyl phosphatidyl choline (1.5 g) were added thereto and stirred at 45° C. for 3 hours, and then cooled. Methanol (20 ml) was added thereto and the organic layer was separated. Furthermore, the aqueous layer was extracted with chloroform (30 ml) and methanol (15 ml). The organic layer was combined and water (20 ml), and methanol (20 ml) was added thereto and partitioned, then the separated organic layer was dried up in vacuo. A mixture of chloroform:ethanol (1:1) (30 ml) was added to the residue and again it was dried in vacuo.

The residue was dissolved in a small amount of chloroform and charged on a flash column of silica gel (Merck, silica gel Art 9385, 4 cm×15 cm) and eluted stepwise with chloroform, then a series of chloroform:methanol mixtures of relative concentrations (20:1), (7:1), (4:1), (3:1) and (2:1), in this order. The eluate was dried up in vacuo to yield a colorless powder of the following structure [Ia] (0.92 g, yield: 50.5%).

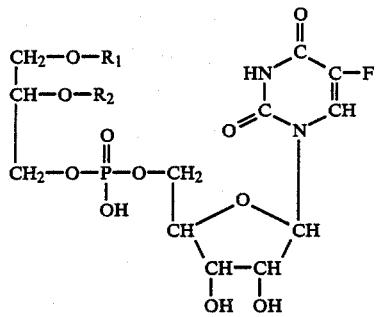

wherein $R_1$ and $R_2$ are palmitoyl.

UV absorption spectrum: $\lambda_{max}=268$ nm (in methanol:chloroform=20:1).

FAB mass spectrum: m/e 915 (M+Na)+

Rf=0.37 (chloroform:methanol:water=65:25:3, Merck Art 5715 plate, spot was detected by UV lamp and molybden-blue; in the following examples, Rf value was measured in the same way.)

Antitumor activity was shown in Table 1.

No acute toxicity was observed at a dose 150 mg/kg i.p. in mice.

EXAMPLE 2

In Example 1 NepA (2.0 g) was used in place of FUR to yield the compound of formula [Ib] (0.31 g, yield: 17.0%)

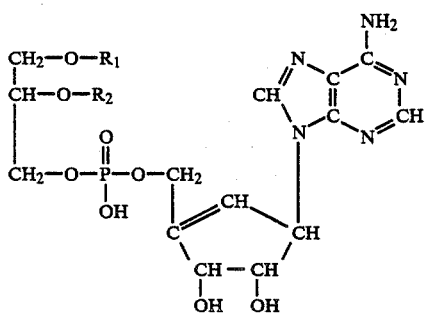

wherein $R_1$ and $R_2$ are palmitoyl.

UV absorption spectrum: $\lambda_{max}=261$ nm (in methanol:chloroform=20:1).

FAB mass spectrum: m/e 894 (MH)+

Rf=0.38.

Antitumor activity of this compound is illustrated in Table 1. No acute toxicity was observed when the compound was administered in amounts of 250 mg/kg body weight.

EXAMPLE 3

Dipalmitoylphosphatidyl choline in Example 1 was replaced by dilinoleoylphosphatidyl choline (1.5 g) to obtain the compound of the formula [Ic] (1.09 g)

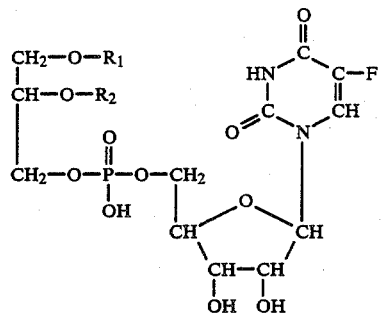

wherein $R_1$ and $R_2$ are linoleoyl.

UV absorption spectrum: $\lambda_{max}=268$ nm (in methanol:chloroform=20:1).

FAB mass spectrum: m/e 963 (M+Na)+

Rf=0.37.

Antitumor activity of this compound is ILS 100.8% (15 kg/mg, 5 times administration, see Table 1) against mouse P-388 leukemia, implanted in the mice, and no acute toxicity at doses 75 mg/kg was observed in the mice.

EXAMPLE 4

5-fluorouridine (FUR, 4.0 g) was added to 100 mM acetate buffer (pH 5.6, 20 ml) containing 100 mM $CaCl_2$ and stirred at 45° C. for 20 mins. Phospholipase D-P (10 mg, Toyo Jozo Co.) and chloroform solution (30 ml) of phosphatidyl choline (egg lecithin, 1.5 g) was added thereto and stirred at 45° C. for 3 hours, and then cooled. After reaction, isolation in the same manner as in Example 1 was performed and the residue was purified with silica-gel chromatography to yield a compound of the formula [Id] (1.11 g).

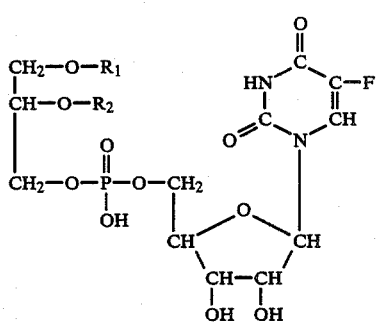

wherein $R_1$ and $R_2$ are radyl.

UV absorption spectrum: $\lambda_{max}=268$ nm (in methanol:chloroform=20:1) Rf=0.37.

Antitumor activity of this compound is ILS 98.3% (15 mg/kg, 5 times administration, see Table 1) against mouse P-388 leukemia, and no acute toxicity at doses 150 mg/kg body weight was observed in the mice.

EXAMPLES 5-8

FUR in Example 1 was replaced by the nucleoside shown in Table 3 to give phospholipid-nucleoside complex [I] which had useful antitumor activities. No acute toxicity at doses 150 mg/kg body weight was observed in the mice.

In Table 3, "*" means that 100 mM acetate buffer (pH 5.6) containing 100 mM calcium chloride (15 ml) was used.

"**" indicates that the process used for recovery of the compound was as follows:

To the reaction mixture after cooling was added methanol (20 ml) to filtrate the insolubles, which were then washed with methanol:chloroform (1:1); the organic layer after separation was washed with sodium chloride solution, filtered through Whatman 1-PS filter paper and dried up in vacuo. The residue was dissolved in a small amount of chloroform and charged on a flash column (Merck, silica gel Art 7747, 4 cm×15 cm) and eluted with chloroform, followed by a series of chloroform:methanol mixtures of relative concentrations (10:1), (7:1), (5:1), (3:1) and (2:1), in this order.

TABLE 3

Example 5:
Nucleoside: FUDR 1.5 g
Dipalmitoyl phosphatidyl choline: 0.75 g
$R_1$ and $R_2$: palmitoyl
Ns: FUDR-5'-yl
Yield: 0.41 g
UV spectrum ($\lambda_{max}$): 268 nm (methanol:chloroform (20:1))
FAB mass spectrum (m/e): 899 (M + Na)+
Rf: 0.44

Example 6:
Nucleoside: bredinin (*) (**) 10 g
Dipalmitoyl phosphatidyl choline: 2.0 g
$R_1$ and $R_2$: palmitoyl
Ns: bredinin-5'-yl
Yield: 1.36 g
UV spectrum ($\lambda_{max}$): 280 nm (methanol:chloroform (20:1))
FAB mass spectrum (m/e): 890 (MH)+
Rf: 0.25

Example 7:
Nucleoside: tubercidine 2.0 g
Dipalmitoyl phosphatidyl choline: 1.0 g
$R_1$ and $R_2$: palmitoyl
Ns: tubercidine-5'-yl
Yield: 0.91 g
UV spectrum ($\lambda_{max}$): 270 nm (methanol:chloroform (20:1))
FAB mass spectrum (m/e): 897 (M + Na)+
Rf: 0.38

Example 8:
Nucleoside: FCR 0.65 g
Dipalmitoyl phosphatidyl choline: 0.73 g
$R_1$ and $R_2$: palmitoyl
Ns: FCR-5'-yl
Yield: 0.33 g
UV spectrum ($\lambda_{max}$): 283 nm, 241 nm (methanol:chloroform (20:1))
FAB mass spectrum (m/e): 914 (M + Na)+
Rf: 0.30

EXAMPLES 9–12

FUR in Example 4 was replaced by the nucleoside shown in Table 4 to obtain phospholipid-nucleoside complex [I] which had useful antitumor activities. No acute toxicity at doses 150 mg/kg body weight was observed.

In Table 4, (*) and (**) have the same meanings as above.

TABLE 4

Example 9:
Nucleoside: FUDR 2.0 g
Phosphatidyl choline: 1.0 g
$R_1$ and $R_2$: radyl
Ns: FUDR-5'-yl
Yield: 0.41 g
UV spectrum ($\lambda_{max}$): 268 nm (methanol:chloroform (20:1))
Rf: 0.44

TABLE 4-continued

Example 10:
Nucleoside: bredinin (*) (**) 10 g
Phosphatidyl choline: 2.0 g
$R_1$ and $R_2$: radyl
Ns: bredinin-5'-yl
Yield: 1.18 g
UV spectrum ($\lambda_{max}$): 280 nm (methanol:chloroform (20:1))
Rf: 0.25

Example 11:
Nucleoside: tubercidin 2.0 g
Phosphatidyl choline: 1.0 g
$R_1$ and $R_2$: radyl
Ns: tubercidin-5'-yl
Yield: 0.71 g
UV spectrum ($\lambda_{max}$): 270 nm (methanol:chloroform (20:1))
Rf: 0.38

Example 12:
Nucleoside: NepA 2.0 g
Phosphatidyl choline: 1.5 g
$R_1$ and $R_2$: radyl
Ns: NepA-6'-yl
Yield: 1.24 g
UV spectrum ($\lambda_{max}$): 261 nm (methanol:chloroform (20:1))
Rf: 0.38

Further examples of starting materials and the phospholipid-nucleoside conjugate products are shown as follows:

| Starting Materials | | Phospholipid-Nucleoside Conjugate | |
|---|---|---|---|
| Phospholipid | Nucleoside | $R_1$ and $R_2$ | Ns |
| Dioleoyl-phosphatidyl-choline | FUR | Oleoyl | FUR-5'-yl |
| Dioleoyl-phosphatidyl-choline | FCR | Oleoyl | FCR-5'-yl |
| Dioleoyl-phosphatidyl-choline | NepA | Oleoyl | NepA-6'-yl |
| Dioleoyl-phosphatidyl-choline | FUDR | Oleoyl | FUDR-5'-yl |
| Dioleoyl-phosphatidyl-choline | Bredinin | Oleoyl | Bredinin-5'-yl |
| Dioleoyl-phosphatidyl-choline | Tubercidine | Oleoyl | Tubercidine-5'-yl |
| Dilinoleoyl-phosphatidyl-choline | NepA | Linoleoyl | NepA-6'-yl |
| Dilinoleoyl-phosphatidyl-choline | FCR | Linoleoyl | FCR-5'-yl |
| Dilinoleoyl-phosphatidyl-choline | FUDR | FUDR-5'-yl | FUDR-5'-yl |
| Dilinoleoyl-phosphatidyl-choline | Bredinin | FUDR-5'-yl | Bredinin-5'-yl |

EXAMPLE 13

Arabinosyl-5-fluorocytosine (783 mg), was dissolved in 100 mM acetate buffer (pH 5.4, 6 ml) containing 100 mM $CaCl_2$ and stirred at 45° C. for 5 mins. Phospholipase D-P (10 mg, from Streptomyces, Toyo Jozo Co., specific activity 160 units/mg) and chloroform solution (20 ml) of dipalmitoyl phosphatidyl choline (367 mg, 0.5 mM) were added thereto and stirred at 45° C. for 3 hours, and then cooled. To the mixture were added 1N HCl (6 ml), chloroform (20 ml) and methanol (20 ml), and the organic layer was separated. The organic layer was washed with water and dried up in vacuo. Ethanol was twice added to the residue and dried up in vacuo each time. The residue was dissolved in a small amount of chloroform, charged on a flash column of silica gel (Merck silica gel Art 9385, 2 cm×12 cm) and eluted stepwise with chloroform, then a series of chloroform-methanol mixtures of relative concentrations (20:1), (10:1), (5:1), (3:1) and (2:1), in this order.

The eluate was dried up in vacuo and the residue was dissolved in chloroform:methanol (2:1) (25 ml), then water was added to separate the organic layer, which was dried up in vacuo to furnish a colorless powder (156 mg, yield: 35.0).

UV absorption spectrum: $\lambda_{max}$=284 nm, 240 nn (in chloroform:methanol=20:1).

FAB mass spectrum: m/e 914 (M+Na)+

Rf=0.31 (chloroform:methanol:water=65:25:3, Merck Art 5715 plate, spot was detected by UV lamp and molybden-blue; in the following examples, Rf value was measured in the same way).

Antitumor activity of this compound has been shown hereinbefore. Furthermore, over 60% ILS was observed when Ehrlich ascites carcinoma, 2×10$^6$ cells/0.2 ml was inoculated intraperitoneally in mice and 2 days thereafter this compound (30 mg/kg) was administered once a day for 7 days. No acute toxicity at doses 150 mg/kg body weight was observed in the mice.

EXAMPLE 14

Arabinosylcytosine (962 mg, 15 equivalents) was dissolved in 100 mM acetate buffer (pH 5.4, 5 ml) containing 100 mM $CaCl_2$ and stirred at 45° C. for 10 minutes. Phospholipase D-P (5 mg) and chloroform solution (10 ml) of L-α-lecithin dioleyl (100 mg, 0.263 mM) was added thereto and stirred at 45° C. for 2 hours, and then cooled. Chloroform (6.6 ml) and methanol (8.3 ml) were added thereto and the organic layer was separated. The organic layer was washed with water (5 ml) and dried up in vacuo. Ethanol (15 ml) was added to the residue and it was dried up in vacuo twice. The residue was dissolved in a small amount of chloroform and charged on a flash column of silica gel (Merck, silica gel Art 9385, 2.5×12 cm) and eluted stepwise with chloroform:methanol (15:1) and (10:1), and further eluted with chloroform:methanol:water (100:10:1), (70:10:1) and (50:10:1) in this order. Eluate was dried up in vacuo and dissolved in chloroform-methanol (2:1) (25 ml), then water (5 ml) was added with vigorous shaking to separate the organic layer, which was dried up in vacuo. Methanol was added thereto and the residue was again dried up in vacuo to give a colorless powder (184 mg, yield: 75.5%).

UV absorption spectrum: $\lambda_{max}$=273 nm (in chloroform:methanol=20:1).

FAB mass spectrum: m/e 948 (M+Na)+

Rf=0.36.

The antitumor activity of this compound has been shown hereinbefore. Further antitumor activity against mice Ehrlich ascites carcinoma was ILS 65.6%. No acute toxicity or mortality at doses of 150 mg/kg body weight was observed in the mice.

EXAMPLE 15

Arabinosyl-5-fluorocytosine was replaced by arabinosyladenine and arabinosylthymine in Example 13 to obtain dipalmitoyl phosphatidyl arabinosyladenine and dipalmitoyl phosphatidyl arabinosylthymine. These compounds have antiviral activity and no mortality was observed at doses of 150 mg/kg body weight in mice. Dipalmitoyl phosphatidyl arabinosyladenine:

UV absorption spectrum: $\lambda_{max}$=259 nm (in chloroform:methanol=20:1).

FAB mass spectrum: m/e 898 (MH)+ and (M+Na)+

Rf=0.39

Dipalmitoyl phosphatidyl arabinosylthymine:

UV absorption spectrum: $\lambda_{max}$=269 nm (in chloroform:methanol=20:1).

FAB mass spectrum: m/e 911 (M+Na)+

Rf=0.46.

TABLE 2

| Nucleoside-Phospholipid Complex [I] | | Tumor | Administration | ILS* |
|---|---|---|---|---|
| $R_1$ and $R_2$ | Ns | Cells | mg/kg (× No.) | (%) |
| Palmitoyl | Arabinosyl-5-fluoro-cytosine-5'-yl | P-388 leukemia | 15 (× 5) | 151.9 |
| Oleoyl | Arabinosyl-cytosine-5'-yl | P-388 leukemia | 30 (× 5) | 153.6 |
| Radyl | Arabinosyl-cytosine-5'-yl | P-388 leukemia | 50 (× 5) | 112.0 |

*Average survival date: P-388 leukemia; 7.57–7.64 days

Examples 16–21:

in Example 1, FUR was replaced by the nucleoside shown in Table 5 and dipalmitoyl phosphatidyl choline was replaced by distearoyl phosphatidyl choline to obtain the compounds of the formula [I] as listed in Table 5.

TABLE 5

| | Starting material | | phospholipid nucleoside conjugate (I) | | | P-388 leukemia treatment | |
|---|---|---|---|---|---|---|---|
| Example | nucleoside (used) | disteroyl phosphatidyl cholin | yield | UV $\lambda_{max}$ | Rf | administration (mg/kg) (× no. of administrations) | ILS (%) |
| 16 | FUR (2.63 g) | 0.79 g | 0.65 g | 268 nm | 0.37 | 30 mg (× 5) | 206% |
| 17 | NeP A (1.60 g) | 0.79 g | 0.38 g | 260 nm | 0.38 | 30 mg (× 5) | 128% |
| 18 | Ara FC (1.3 g) | 0.79 g | 0.44 g | 285 nm | 0.31 | 30 mg (× 5) | 194% |
| 19 | Ara C (3.6 g) | 0.79 g | 0.48 g | 273 nm | 0.36 | 30 mg (× 5) | 160% |
| 20 | FUDR (3.3 g) | 0.79 g | 0.40 g | 268 nm | 0.44 | 30 mg (× 5) | 36% |
| 21 | Bredinin (5.0 g) | 0.79 g | 0.26 g | 280 nm | 0.25 | — | — |

What is claimed is:

1. A compound of the formula

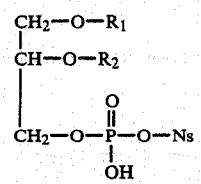

wherein $R_1$ and $R_2$ are long-chain fatty acid residue, and Ns is neplanocin A-6'-yl- or a nucleoside residue selected from the group consisting of 5-fluorouridine-5'-yl, and arabinocyl-5-fluorocytosine-5'-yl-, and pharmacologically acceptable salts thereof.

2. Compound according to claim 1 wherein $R_1$ and $R_2$ are palmitoyl and Ns is 5-fluorouridine-5'-yl- or a pharmocologically acceptable salt thereof.

3. Compound according to claim 1 wherein $R_1$ and $R_2$ are palmitoyl and Ns is neplanocin A-6'-yl- or a pharmacologically acceptable salt thereof.

4. Compound according to claim 1 wherein $R_1$ and $R_2$ are stearoyl, and Ns is 5-fluorouridine-5'-yl- or a pharmacologically acceptable salt thereof.

5. Compound according to claim 1 wherein $R_1$ and $R_2$ are stearoyl, and Ns is neplanocin A-6'-yl- or a pharmacologically acceptable salt thereof.

* * * * *